United States Patent [19]

Stenzler

[11] 4,351,344

[45] Sep. 28, 1982

[54] METHOD AND APPARATUS FOR MONITORING LUNG COMPLIANCE

[75] Inventor: Alex Stenzler, Syosset, N.Y.

[73] Assignee: Bio-Med Devices, Inc., Stamford, Conn.

[21] Appl. No.: 206,393

[22] Filed: Nov. 13, 1980

[51] Int. Cl.³ ............................................. A61B 5/08
[52] U.S. Cl. ................................................ 128/720
[58] Field of Search ................... 128/720, 716, 204.22, 128/204.23, 205.23

[56] References Cited

U.S. PATENT DOCUMENTS 3,678,296 7/1972 Day ..................................... 128/720
4,031,885 6/1977 Davis et al. ......................... 128/720
4,036,222 7/1977 Gillard et al. ....................... 128/720

OTHER PUBLICATIONS

Saklad et al., "Obtaining and Interpreting Respiratory Flow, Pressure and Waveforms", Journal of International Anesthesiology Clinics, vol. 12, pp. 25-45, 1974.
Galvis et al., "Continuous Dynamic Monitoring of Pressure Flow Patterns During Assisted Ventilation", Journal of Pediatric Surgery, vol. 11, No. 3, Jun. 1976, p. 307.
Specht et al., "Monitoring of Pressure-Limited Neonatal Ventilators", Respiratory Care, vol. 23, No. 1, Jan. 1978, pp. 74 and 76.
Reynolds et al., "A Multiplex Cathode-Ray-Tube Display with Digital Readout for a Body Plethysmograph", Medical and Biological Eng. vol. 11, No. 3, May 1973, pp. 268-274.

Primary Examiner—Henry J. Recla
Attorney, Agent, or Firm—St. Onge, Steward, Johnston & Reens

[57] ABSTRACT

Respirator techniques are described for measuring the linear slope of the inspiratory phase to monitor lung compliance. The measurements of the slope characterize a pressure wave index which is recorded at regular intervals to provide a clear record from which a warning of the patient's pulmonary condition such as lung compliance can be derived. Several techniques are shown and described. In one, the pressure wave index is determined by sensing the times when the pressure-time signal reaches predetermined pressure levels above a base line. In another technique, the linear slope segment is searched for and its slope then measured.

19 Claims, 9 Drawing Figures

| | FREQ. (IMV) | INSPIR. TIME (SEC) | EXPIR. TIME (SEC) | PEAK CM$H_2O$ | MEAN | PEEP | PWI (MS.) |
|---|---|---|---|---|---|---|---|
| BEFORE | 28 | .56 | 1.58 | 23.9 | 9.2 | 4.0 | 58 |
| AFTER | 28 | .56 | 1.58 | 23.9 | 9.2 | 4.0 | 34 |

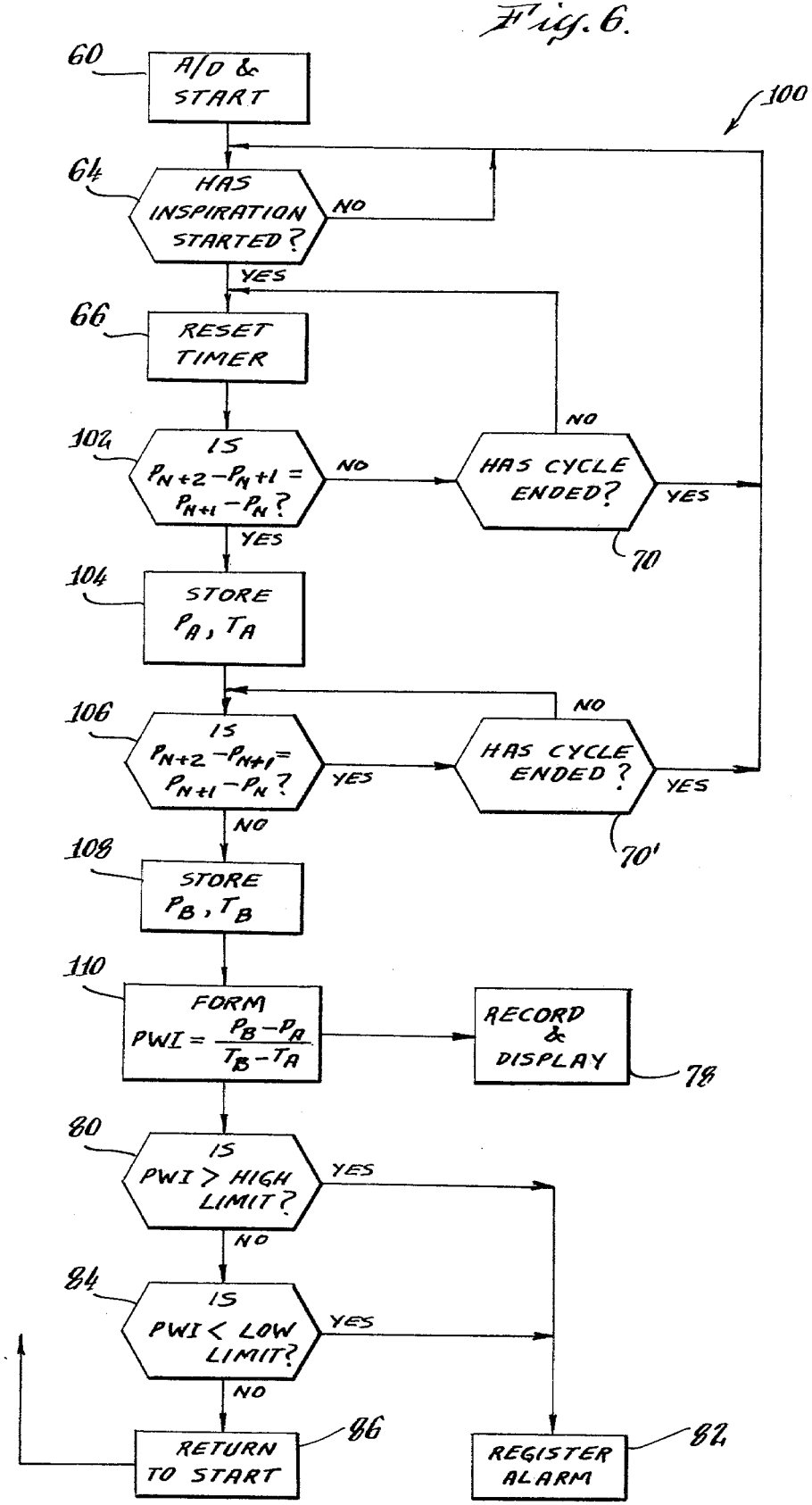

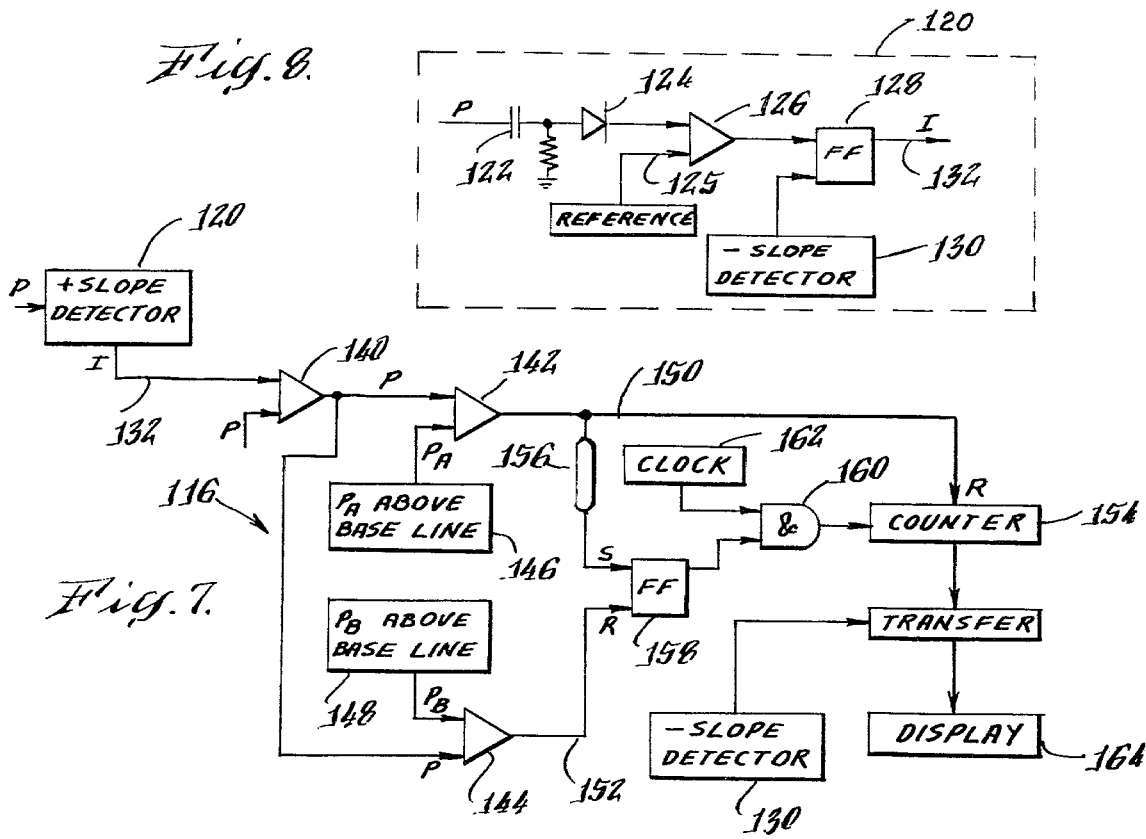
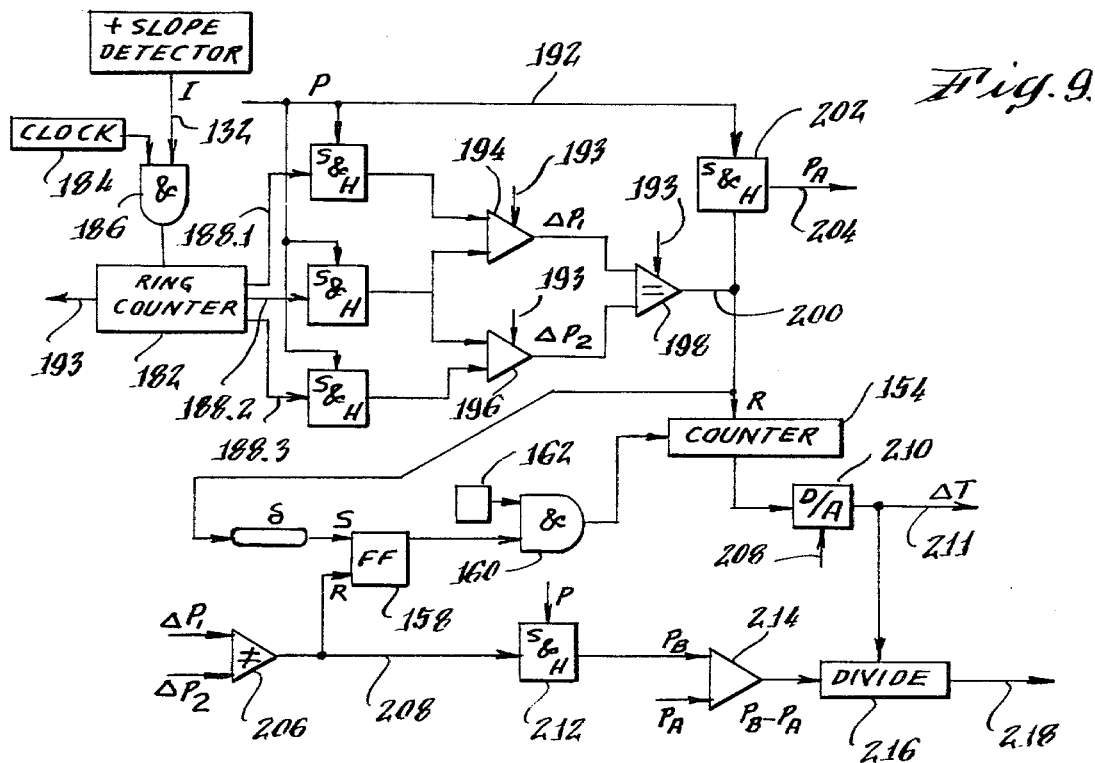

METHOD AND APPARATUS FOR MONITORING LUNG COMPLIANCE

FIELD OF THE INVENTION

This invention relates to respirators and respirator monitors generally and more specifically to a determination of the compliance of the lungs of a patient on a respirator.

BACKGROUND OF THE INVENTION

In the field of respirators, a supply of air is provided to a patient, usually with inspiratory and expiratory cycles to aid the patient's breathing cycle. The air is supplied at a mouthpiece or through a breathing tube into the lungs and the pressure of the airway to the patient is monitored with a pressure sensor which is pneumatically coupled to the airway. The output from the pressure sensor may be an electrical signal which may be recorded for monitoring of the patient and may be used in various control functions in the respirator.

Mechanical ventilation for respiratory distress syndrome has relied heavily on constant flow, time cycled respirators. In most neonatal and pediatric intensive care centers these respirators are pressure limited with sufficient flow rates to achieve a square pressure waveform. A major limitation in pressure limited ventilation is that volume is unknown and thus sudden changes in compliance, such as occur following accidental pneumothorax or endobronchial intubation, may escape detection until a change in the patient's condition becomes clinically evident.

It has been recognized that the pressure signal from the pressure sensor represents various phases of the patient's breathing cycle. For example, with reference to an article entitled "Obtaining and Interpreting Respiratory Flow, Pressure and Volume Waveforms" by M. Saklad et al, published in the Journal of the International Anesthesiology Clinics, Volume 12, pages 25-45, 1974 an upper airway pressure wave form is shown on page 30 and which is similar to the waveform at 8 in FIG. 2 herein. The pressure-time waveform is characterized by an inspiration phase commencing at a time $t_1$ at a baseline 10 and increasing to a peak at 12 and a plateau 14. At about a time $t_2$, the inspiration phase ends and expiration begins following a waveform as shown, to baseline 10 until a successive inspiration phase begins at a time $t_3$. As indicated at page 40 of this article, the portion of the inspiration phase characterized by the sloped segment of the inspiratory pressure waveform segment 16 is related to the compliance of the lung and chest wall when the pressure at the patient airway is being monitored. Hence, in a pressure limited, time cycled ventilation the lung is exposed to a pressure head and will fill with a volume of air dependent upon lung compliance.

The desirability and benefit of continuous, dynamic monitoring of the airway pressure signal from patients requiring ventilating assistance and, in particular, infants and children, is noted in an article entitled "Continuous Dynamic Monitoring Of Pressure And Flow Patterns During Assisted Ventilation" by A. G. Galvis et al, published in the Journal of Pediatric Surgery Vol. 11, No. 3, (June) 1976 at page 307.

The latter article provides a technique for displaying pressure waves, such as 8 in FIG. 2, on an oscilloscope and teaching personnel how to recognize and identify problems from the displayed waveforms. Such monitoring program, though effective, does not readily permit recognition of breathing difficulties or gradual degeneration attributable to an alteration in compliance unless these are characterized by visually distinct increase in waveform amplitude.

In an article by W. Specht et al entitled "Monitoring of Pressure-limited Neonatal Ventilators" published in Respiratory Care of January 1978, Vol. 23, No. 1 at pages 74, 76, it is recognized that the slope of the pressure wave signal represents lung compliance and, therefore, observation of the pressure-time relationships in neonates may be clinically useful in determining ventilator management. The slope measuring from an oscilloscope display or chart-recording of the pressure wave signal, however, not only is tedious but also does not provide an accurate and reliable basis for monitoring the lung compliance of the patient so that a rapid diagnosis is often needed for acute complications such as a pneumathorax condition is not available.

SUMMARY OF THE INVENTION

With a respirator in accordance with the invention, the patient's lung compliance can be monitored and significant changes rapidly detected. As described with reference to one form for determining a patient's lung compliance in accordance with the invention, a pressure signal is used. The pressure signal represents the airway pressure or such other patient pressure monitored by a pressure sensor pneumatically coupled to the tube through which air is supplied from a respirator.

The pressure signal is applied to a network which detects the start of the inspiratory phase of the patient's breathing cycle and then effectively measures the slope of a linear portion of the inspiratory segment of the pressure signal.

The slope may in one embodiment be measured by determining the time duration between two predetermined pressure levels which normally lie along the linear portion. In another embodiment, the slope of the linear portion is measured by detecting when the linear portion starts and ends and storing the pressure amplitudes at the start and end of the inspiratory phase.

The measurement of the slope of the linear portion results in a signal, defined as a pressure wave index signal, whose magnitude characterizes the patient's lung compliance. When the pressure wave index is so automatically measured for the patient at regular intervals, small and physiologically significant alterations of the patient's lung compliance can be accurately and reliably detected so that early corrective procedures can be implemented.

For example, in some infant patients a pneumothorax condition (a rupture of a lung) may occur, which would still allow normal cycling of the respirator, though an acute condition for the patient now exists. In the normal recording of pressure-time waveforms of breathing cycle on oscilloscopes or chart recorders, inspiratory slope changes due to a pneumothorax condition are difficult to detect, and certainly gradual but significant changes occurring over a long time period are not easily detected. With an automatic compliance measuring technique in accordance with the invention, the resulting change in the pressure wave index signal or lung compliance may be promptly detected and an alarm registered to alert the professional staff to take corrective action.

When in the use of a respirator, a nasotracheal tube slips or a kink developes in an endotracheal tube, the pressure wave index signal shows dramatic changes in value which may be promptly sensed to provide a warning.

A periodic monitoring and recording of the pressure wave index signal for the patient provides a particularly effective and clear numerical record of the patient's lung compliance without having to study and laboriously compare difficult to read waveforms on an oscilloscope or a chart recorder.

It is, therefore, an object of the invention to provide a method and apparatus for determining the lung compliance of a patient. It is a further object of the invention to provide a method and apparatus for monitoring the lung compliance of a patient and promptly register an alarm when such compliance varies significantly.

BRIEF DESCRIPTION OF DRAWINGS

FIG. 6 is a block diagram of another technique for monitoring lung compliance in accordance with the invention;

FIG. 7 is a schematic and block diagram of a system for monitoring a patient's lung compliance in accordance with the invention;

FIG. 8 is a schematic and block diagram for generating a signal representative of the duration of the inspiratory phase of a breathing cycle;

FIG. 9 is a schematic and block diagram for another system for generating a pressure wave index signal indicative of the lung compliance of a patient.

DETAILED DESCRIPTION OF DRAWINGS

Figure 1:
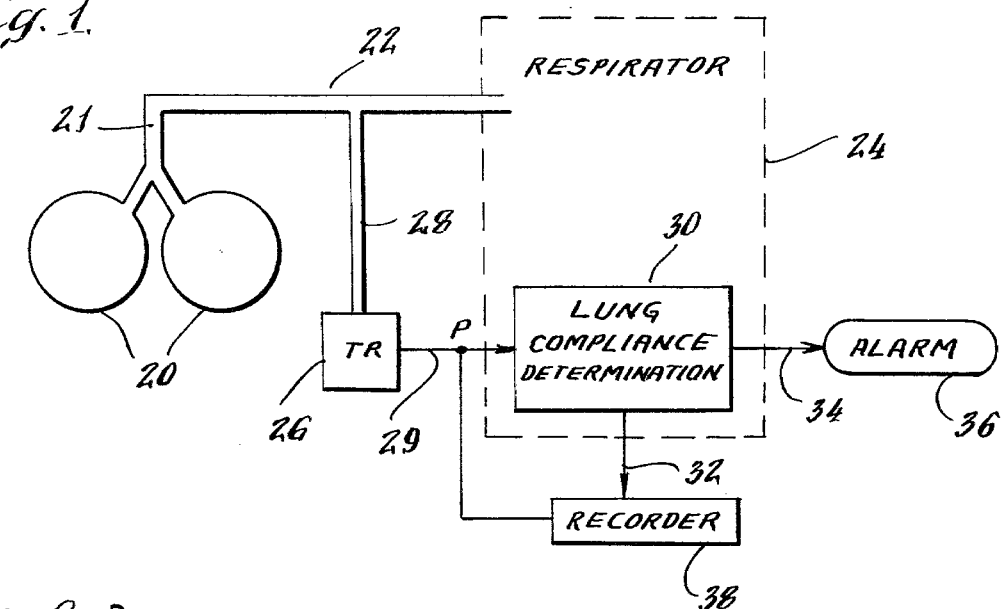
FIG. 1 is a block diagram of a lung compliance monitoring system in accordance with the invention.

With reference to FIG. 1, a patient is schematically designated with his or her lungs 20 and connected through the patient's airway 21 and appropriate air tubing 22 to a respirator 24. The patient may be an adult supplied air through a proximal airway connector (not shown). In the embodiment illustrated in FIG. 1, it is assumed that the patient is an infant. The respirator 24 may be of various types. However, for purposes of the description respirator provides the infant patient with a time cycled, continuous flow of air which is pressure limited and supplied in inspiratory and expiratory phases.

A pressure transducer 26 is pneumatically coupled through a tubing 28 to the patient airway to produce a pressure signal, P, on line 29. Pressure signal P represents the patient airway pressure. The term pressure signal as used herein, therefore, encompasses such variations in pulmonary respiratory procedures.

The respirator 24 may have a variety of controls as are well known in the art such as selection of the inspiration to expiration ratio, (I/E), frequency of breathing cycles in number per minute, individual selection of inspiration and expiration times, peak pressure supplied to the patient in cm of water, and positive end expiratory pressure (PEEP) also in cm of water.

The pressure signal P may be used in respirator 24, but for clarity is shown coupled to a lung compliance monitoring device 30. The latter generates on line 32 a pressure wave index (PWI) signal or compliance signal representative of the patient's lung compliance and depending upon whether the PWI signal exceeds certain limits provides a compliance alarm signal on line 34. The compliance alarm signal may be applied to a bell or light or other alarm registering device 36.

The pressure wave index signal is, in effect, a measurement of the slope of the inspiratory pressure signal and may be expressed as cm per millisecond, or only in milliseconds when only the time between predetermined pressures levels is measured.

The PWI or compliance signal on line 32 is applied to a storage device 38 such as a recorder which enables one to form a time history of the lung compliance of the patient and thus provide an easily read warning record to detect slowly occurring degradations or improvements in the patient's pulmonary condition.

It is understood that in certain patients the compliance being measured includes the entire chest wall with airway 21 as well as lungs 20. The term lung compliance or compliance as used herein is intended to encompass all such compliance measurements. Generally, however, and particularly with neonatals the pressure wave index signal represent the compliance of the patient's lungs.

Figure 3:
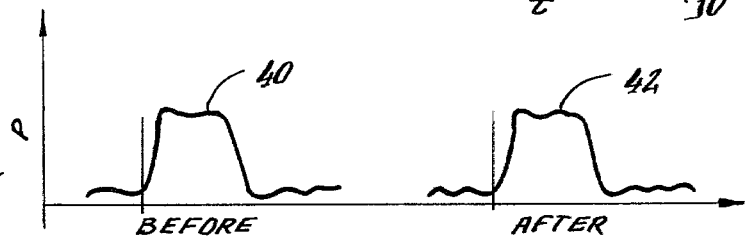
FIG. 3 are pressure-time waveforms of a patient prior to and subsequent to the onset of a pneumothorax condition with a corresponding tabulation of respirator settings and the patient's lung compliance as represented by pressure wave index measurements.

With the monitoring of lung compliance in accordance with the invention, a warning may be registered in a visually clear manner as may be appreciated with reference to FIG. 3. In this figure a pair of pressure waveforms 40, 42 are shown respectively illustrating a normal patient breathing cycle with waveform 40 and an abnormal breathing cycle with waveform 42 after the patient has suffered a pneumothorax. The waveforms 40, 42 look very similar, even when recorded on a chart carrying close rectangular plotting lines and to one trained to recognize inspiratory slope changes. When, however, the slope of segment 16 is measured with device 30, a precise value for the slope of the pressure wave index (PWI) value in milliseconds such as 58 ms (see table in FIG. 3) is obtained for pressure waveform 40 and 34 ms for waveform 42.

The dramatic change in value from 58 to 34, or about 40%, can be readily detected and when recorded provides a clear warning of a serious pulmonary change of the patient.

The lung compliance determining device 30, however, may also include suitable control limits with which the measured pressure wave index value is compared. For example, when the PWI signal drops below about 10% of the normal value of 48 ms, a warning in the form of an actuation of alarm 36 may be produced to alert the professional staff of a degenerating pulmonary condition. Similarly, when, for example, the ventilator tube 22 is shifted or encounters an unexpected obstruction, the pressure wave index value tends to decrease abnormally when measured in milliseconds. Such abnormal decrease may be detected by comparing the PWI signal with a low limit and recording a warning when such condition arises.

Figure 2:
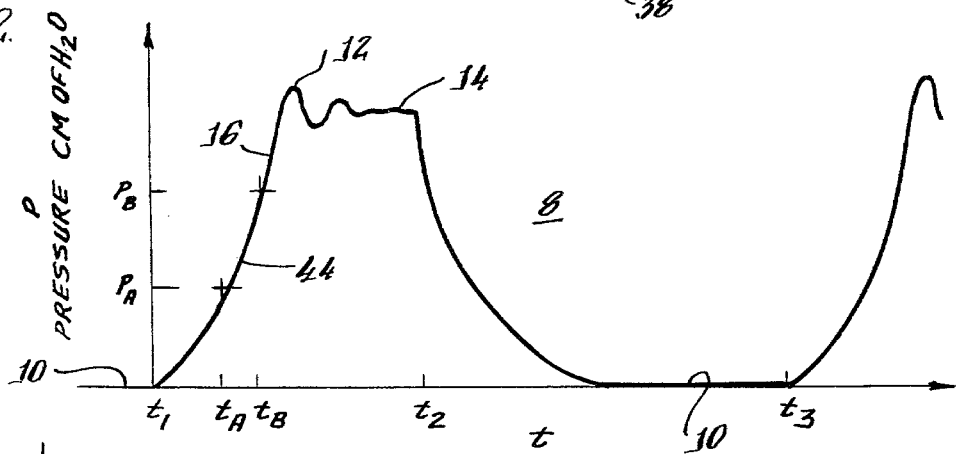
FIG. 2 is a pressure-time waveform for pressure signal from a breathing cycle assisted with a respirator.

The compliance determining device 30 functions in close cooperation with respirator 24 and may be formed with a variety of hardware techniques. A desirable characteristic is that the device 30 can automatically locate the start of an inspiratory phase such as at $t_1$ and $t_3$ in FIG. 2 and can then automatically determine the slope (PWI) of a mid portion 44 during which the pressure P varies linearly with time t. In FIG. 2 the linear mid portion 44 may extend between the pressure limits $P_A$ and $P_B$ and times $t_A$, $t_B$.

The device 30 may be formed with discrete circuits or may use a programmed microprocessor also employed to perform other functions in respirator 24. The pressure signal P from pressure transducer 26 (see FIG. 1) is sampled and the samples converted to digital values as a function of time for use in a microprocessor or computer as at step 60 in the flow chart 62 shown in FIG. 4. The function of device 30 may be performed by a microprocessor dedicated to the measurement of pressure wave index values for the inspiratory phases of sequential breathing cycles or part of a microprocessor operation for controlling a respirator such as 24. The functions of devices 30 may also be performed by a general purpose computer.

Figure 4:
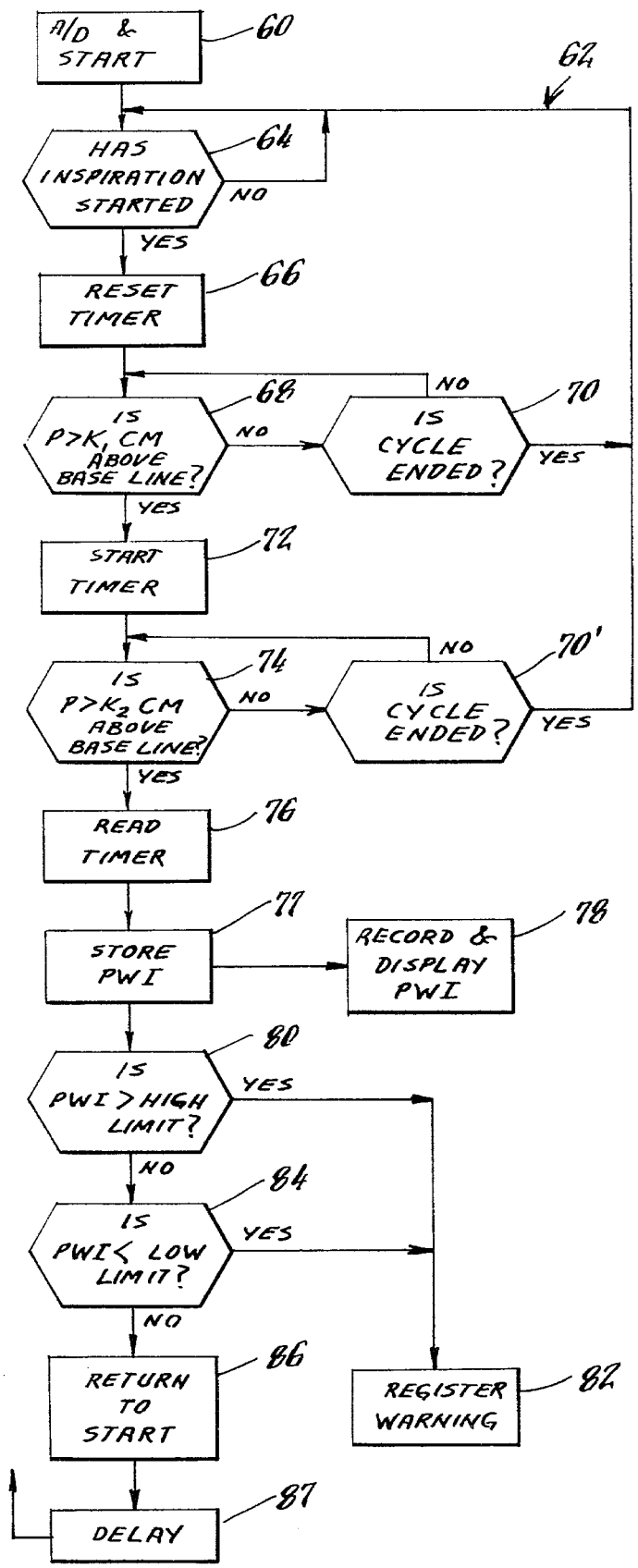
FIG. 4 is a block diagram of one technique for measuring lung compliance in accordance with the invention.

With reference to FIG. 4, sampling and conversion to digital values is obtained at a sufficiently high sampling rate so that the digital values accurately represent pressure-time waveforms such as 8. Normally, since the sampling rate is known, the time t of any one sample in the waveform is also known; however, the determination of the compliance or measurement of the pressure wave index is carried out in real-time in flow chart 62 as a pressure time waveform 8 is generated. A test is performed at 64 as to when, within the samples of pressure waveform 8, the inspiratory phase starts. Such test may be carried out by comparing successive pressure values until they descend to a minimum value and then again begin to increase.

At 66 a timer is reset to a first time indicating level. Typically, this involves a resetting of a counter which is supplied with clock pulses in synchronization with normal time. Then at 68 a test is made when a pressure sample represents a predetermined level above the pressure level at the start of the inspiratory phase; i.e. above the base level 10 of a pressure waveform as shown in FIG. 2. This predetermined level is selected so that when the test 68 is met by a sample, it is in the linear portion 44 of a pressure waveform 8.

The actual level may vary and is expressed in cm of water. In practice, a pressure level equivalent to about 5 cm of water from baseline 10 is sufficient to locate the sample in the linear segment 44 of inspiratory pressure-time waveform 16. The test 68 is run until either it is satisfied at a time $t_A$ or the cycle of operation is ended under limits at 70.

When the test 68 is satisfied, the timer or counter is started at 72 until the pressure waveform 8 attains a second predetermined level $P_B$ above the base level 10 (see FIG. 2). The level $P_B$ is selected so that the sample which satisfies test 74 lies within linear portion 44 of segment 16 of the inspiratory phase. In practice, the level $P_B$ was selected at a pressure equivalent to about 10 cm of water above baseline 10.

Once test 74 is satisfied, the timer is read at 76 to yield a second time signal $t_B$ and this is stored at 78. The difference in time between $t_B$ and $t_A$ represents the pressure wave index PWI. In the arrangement of FIG. 4, the value of $t_A$ was set at zero and, therefore, the value of the timer reading at 76 represented a measurement of compliance of the lungs, PWI in units of time such as milliseconds.

The value for PWI is stored at 77 and recorded and displayed at 78 to provide a visual record or retrievable history of the patient's lung compliance and enables an early warning of pulmonary disorders or precise record from which an improvement may be diagnosed.

Of particular value in the determination of lung compliance with the PWI measurement is the ability to warn of excessive values. At 80 the value of PWI is compared to a high limit. If the limit is exceeded, a warning in the form of light or sound alarm is registered at 82. The high limits may be selected in terms of absolute values or as a certain percentage value above the patient's actual performance.

Similarly, at 84 the PWI value stored at 77 is compared to a low limit. If the PWI value has dropped below this limit, a warning is generated at 82. Selection of a low limit may be determined similarly to the high limit at 80.

A return is then made at 86 to the start at 60 for the next breathing cycle. This return may be made immediately to examine the next inspiratory phase, or the return may be delayed for such time as is deemed appropriate by setting a suitable delay at 87. The measurement of the pressure wave index is thus carried out at regular intervals which thus may vary between successive inspiratory phases or longer intervals measured in minutes or hours.

Figure 5:
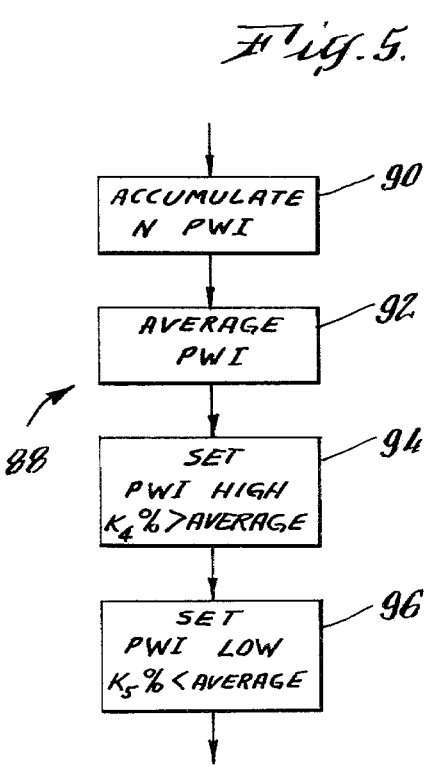
FIG. 5 is a block diagram for a technique for setting upper and lower limits for pressure wave index measurements.

In FIG. 5 a technique 88 is shown to establish the high and low limits. At 90 the values of the pressure wave index, PWI are accumulated for a predetermined number N. An average PWI value is then obtained at 92 by dividing the accumulated value by N. The high limit is thereupon determined at 94 by selecting a predetermined percentage greater than the average value and similarly the low limit is determined at 96 by selecting a predetermined percentage smaller than the average. In practice, these percentages may be of the order of between about 20% to about 50% on either side of the average normal PWI level for that patient though other ranges may be selected.

The measurement of the pressure wave index may be made at periodic intervals such as ten minutes and each measurement may represent the averaging of a number of such measurements. The PWI values may be stored and then recalled for subsequent diagnosis.

FIG. 6 illustrates another technique 100 for measuring the slope of linear portion 44 (see FIG. 2) of inspiratory phase 16. In this technique a search is made for the time and pressure values when the inspiratory phase 16 first appears linear. A search is then made for the time and pressure values when the inspiratory phase 16 again exhibits non-linear behavior such as above linear portion 44.

Thus, with reference to FIG. 6 wherein steps similar to those described with reference to FIG. 4 are given the same number designation, at 102 a test is made when the amplitude difference between three successive samples which are spaced at equal time intervals, becomes equal. When the test is satisfied, the most recent sample which caused satisfaction of the sample test is selected and its pressure value, $P_A$ and time value $T_A$ are stored at 104.

Then at 106 a similar test is made, except a search is performed when the difference between three successive samples first becomes unequal or different. This time the oldest sample in the group which satisfied the test 106 is selected and its pressure value $P_B$ and time value $T_B$ are stored at 108.

A calculation is then made at 110 to measure the slope or pressure wave index according to the well known slope formula $PWI=(P_B-P_A)/(T_B-T_A)$. The PWI value is stored, recorded and displayed at 78.

The technique 100 for determining the time location of the linear portion 14 may be carried out with more than three samples. The number selected is determined by the sampling rate and resulting accuracy.

FIGS. 7 and 8 illustrate discrete circuits 116, 118 for performing the technique as illustrated in FIG. 4. The pressure signal P is shown applied to positive slope detector 120 which may take the form as illustrated in FIG. 8. Thus, the pressure signal P is applied through a differentiating capacitor 122 and appropriately oriented diode 124 to an analog logic gate 126. When the amplitude from diode 124 exceeds a certain reference value on line 125, gate 126 produces an output to set a flip-flop 128. A negative slope detector 130 detects the beginning of the expiratory phase and resets flip-flop 128. The latter's output line 132, therefore, generates a signal I whose duration is generally that of the inspiratory phase 16 (see FIG. 2) between times $t_1$ and $t_2$.

In FIG. 7 the pressure signal P is applied to an input of an analog logic gate 140, together with enabling line 132 so that during inspiration, the pressure signal P is applied to both analog gates 142, 144. Reference values $P_A$ and $P_B$ from sources 146, 148 respectively are applied to gates 142 and 144 to thus provide output signals on lines 150, 152 in the form of pulses with pulse generators (not shown) incorporated in gates 142, 144.

The pulse on line 150 is first effective to reset a counter 154 and after a slight delay from network 156, set a flip-flop 158. This, in turn, enables an AND gate 160 to allow a clock 162 to enter pulses into counter 154.

When the pressure signal P exceeds the value $P_B$, a pulse on line 152 resets flip-flop 158 and thus disables AND gate 160 to stop counter 154. The counter 154 now contains a measurement of the slope or PWI. Upon the detection of the expiration phase by negative slope detector 130, the PWI value in counter 154 is transferred to a display 164 and if desired, to a suitable recorder (not shown).

The network 180 shown in FIG. 9 may determine lung compliance or measure the pressure wave index value PWI using a technique as shown in FIG. 6. A ring counter 182 is actuated from the beginning of an inspiration phase by a clock 184 whose pulses are applied to AND gate 186 to ring counter 182. The ring counter generates at equal intervals three pulses on lines 188.1, 188.2 and 188.3 and in respective succession. The latter lines are applied to three sample and hold networks 190.1, 190.2 and 190.3, each of which samples pressure signal P on line 192.

The sampled pressures are briefly compared at the end of the sampling cycle with a sync signal on line 193 from ring counter 182 with comparators 194, 196 whose outputs $\Delta P_1$, $\Delta P_2$ are tested for equality with an analog logic gate 198. When such equality occurs, a pulse is generated on output line 200 to activate sample and hold network 202. The latter samples pressure line 192 and thus generates on output 204 a signal equal to pressure $P_A$ at the start of the linear portion 44 (see FIG. 2).

At the same time, line 200 resets a counter 154 and after a slight delay sets flip-flop to start counter 154 as described with reference to FIG. 7. When thereafter, at the top of linear pressure waveform portion 44, the values $P_1$ and $P_2$ are no longer equal, as sensed by analog logic gate 206 on output 208, the flip-flop 158 is reset and the value in counter 154 converted to an analog value with a digital to analog converter 210. The latter's output 211 represents the value $\Delta T$ or the duration of the linear portion 44. The value $P_B$ at the end of the linear portion is obtained with a sample and hold network 212 actuated by the pulse signal on line 208.

The slope or PWI of linear portion 44 is then determined by forming the difference $P_B-P_A$ with difference amplifier 214 and dividing this by the value $\Delta T$ in divider 216. The output 218 of divider 216 then represents a determination of lung compliance or a measurement of the pressure wave index.

Having thus described several techniques for monitoring lung compliance when a patient is on a respirator, the advantages of the invention can be appreciated. Continuous monitoring of the pressure wave index enables a sensitive non-invasive technique for evaluating patient ventilation and detection of sudden changes in compliance. Variations from the described embodiment can be made without departing from the scope of the invention.

What is claimed is:

1. A device for deriving an indication of the compliance of a patient's lungs while a respirator provides a supply of gas to the patient and with the use of a pressure sensor operatively coupled to the patient's airway to produce a pressure signal represenatative of the patient's airway pressure as a function of time during the inspiratory phase of the breathing cycle and wherein a slope of the pressure signal during the inspiratory phase is representative of the compliance of the patient's lungs, comprising:
   means responsive to the pressure signal for periodically effectively measuring said slope for respectively different breathing cycles and generating pressure wave index signals representative thereof as indicative of the compliance of the patient's lungs; and
   means responsive to said pressure wave index signals to register an indication thereof.

2. The device as set forth in claim 1 wherein said means for registering said further includes
   means for recording said pressure wave index signals.

3. The device as set forth in claim 1 wherein said means for registering said indication further comprises
   means responsive to said pressure wave index signals for sensing when said slope of the pressure signal is representative of an alarm breathing condition and generating a signal indicative thereof.

4. The device as set forth in claim 1, 2 or 3 wherein said slope measuring means further comprises:
   means responsive to said pressure signal for detecting a starting time of the inspiratory phase at a base pressure level; and
   means referenced with respect to said detected starting time for determining the location of a linear portion in said pressure signal.

5. The device as set forth in claim 4 wherein said means for determining the time location of said linear portion further comprises:
   means for sensing, after the detected start of the inspiratory phase, when said pressure signal increases a predetermined amount above said base pressure level occurring at the start of said inspiratory phase and generating a first time signal representative thereof, wherein said predetermined amount is selected commensurate with that needed to obtain a first time location of said linear portion.

6. The device as set forth in claim 5 wherein said slope measuring means further comprises:
    means for detecting when the pressure signal has increased to a second predetermined level above said base pressure level and producing a second time signal representative thereof; and
    means for determining the time difference between said first and second time signals as said pressure wave index signal for the inspiratory phase.

7. The device as set forth in claim 5 wherein said slope measuring means further comprises:
    means for measuring the slope of said pressure signal following said first time signal and generating said pressure wave index signal therefrom as an indication of the compliance of the lungs of the patient.

8. The device as set forth in claim 4 wherein said means for determining the location of said linear portion further comprises:
    means for measuring the slope of incremental segments of the pressure signal following the detected starting time of the inspiratory phase;
    means for comparing slope measurements between sequentially occurring incremental segments of the pressure signal, and generating a first signal when successive slope measurements are substantially the same.

9. The device as set forth in claim 8 wherein said means for measuring the slope of said linear portions further includes
    means for comparing slope measurements between sequentially occurring incremental segments of the pressure signal following generation of the first signal and generating a second signal when successive slope measurements are not substantially the same; and
    means for determining as said pressure wave index signal, the slope of the pressure signal occurring between said first and second signals.

10. The device as set forth in claim 8 wherein said means for measuring the slope of said linear portion further includes
    means for measuring a first pressure of said pressure signal at a time represented by the first signal;
    means for sensing when said pressure signal has increased to a predetermined level above said first pressure and generating a second signal indicative thereof; and
    means for determining the time difference between said first and second signals as indicative of said pressure wave index signal and the compliance of the lungs of said patient.

11. A method for deriving an indication of the compliance of a patient's lungs while providing a supply of air to the patient with a respirator having a pressure sensor used to produce a pressure signal representative of the patient's airway pressure as a function of time during the inspiratory and expiratory phases of the patient's breathing cycle and wherein the slope of a linear portion of the pressure signal during the inspiratory phase is representative of the compliance of the patient's lungs, comprising the steps of:
    periodically effectively measuring the slopes of the linear portions of the inspiratory phases of the pressure signals as they are generated by the pressure sensor while a patient is connected to the respirator, and generating pressure wave index signals representative of the magnitude of said slopes; and
    recording the pressure wave index signals to form a warning record of the patient's lung compliance.

12. A method as set forth in claim 11 wherein said step for measuring the slope further comprises:
    measuring the time interval between first and second predetermined pressure levels in said pressure signals as said pressure wave index signals.

13. A method as set forth in claim 11 wherein said step for measuring the slope further comprises the steps of:
    periodically comparing the slopes between sequentially occurring incremental portions of the pressure signal until at a first pressure and first time said slopes are substantially the same and thereafter initially different at a higher second pressure and later second time; and
    determining the slope of said pressure signal between said first and second pressures and times as said pressure wave index signal.

14. A method as set forth in claim 11, 12 or 13, wherein said recording step further comprises the steps of:
    forming upper and lower limit values for said pressure wave index signals; and
    comparing said pressure wave index signals with said upper and lower limits to generate a warning when said pressure wave index signals with said upper and lower limits to generate a warning when said pressure wave index signal exceeds the upper limit or drops below said lower limit.

15. A method as set forth in claim 14 wherein said step for forming said upper and lower limit values further comprises:
    averaging a preselected number of sequential pressure wave index signals;
    selecting said upper limit a value which is a predetermined percentage above said averaged pressure wave index signal; and
    selecting as said lower limit a value which is a predetermined percentage below said averaged pressure wave index signal.

16. A device for deriving an indication of the compliance of a patient's lungs with a respirator for providing a supply of air to a patient with the use of a pressure sensor operatively coupled to the patient's airway to produce a pressure signal representative of the patient's airway pressure as a function of time during the inspiratory phase of the breathing cycle and wherein the slope of a linear portion of the pressure signal during the inspiration phase is representative of the compliance of the patient's lungs, comprising:
    means responsive to the pressure signal for periodically effectively measuring the slopes of said linear portion of the inspiratory phases of the patient's breathing cycles and generating pressure wave index signals respectively representative of said measured slopes and the compliance of the patient's lungs during respective breathing cycles;
    means for detecting when a said pressure wave index signal represents a lung compliance measurement indicative of a significant alteration of the compliance of the patient's lungs and generating a warning signal indicative thereof; and means for registering said warning signal to indicate said significant alteration in the patient's lung compliance.

17. A device as set forth in claim 16 wherein said detecting means further comprises:
   means for producing upper and lower limit values for said pressure wave index signals; and
   means for comparing said measured pressure wave index signals with said upper and lower limit values and generating said warning signal when the pressure wave index signal respectively exceeds or drops below said upper and lower limit values.

18. A device as set forth in claim 17 wherein said means for producing the upper and lower limit values further comprises:
   means for producing a signal representative of the average of a predetermined number of measured pressure wave index signals;
   means for forming said upper limit value at a predetermined percentage above said averaged pressure wave index signal; and
   means for forming said lower limit value at a predetermined percentage below said averaged pressure wave index signal.

19. In a respirator for providing a supply of air to a patient with the use of a pressure sensor to produce a pressure signal representative of the patient's airway pressure as a function of time during the inspiratory phase of the patient's breathing cycle and wherein the slope of a linear portion of the pressure signal during the inspiratory phase is representative of the compliance of the patient's lungs, the improvement comprising:
   means responsive to the pressure signal for effectively measuring the slope of said linear portion of the inspiratory phase of the patient's breathing cycle and generating pressure wave index signals respectively representative of said measured slopes and the compliance of the patient's lungs during respective breathing cycles;
   means responsive to the pressure wave index signal during a selected time period for generating a reference level thereof;
   means for comparing pressure wave index signals measured subsequently to said selected time period with the reference level for producing a warning signal when pressure wave index signals deviate from said reference level by a predetermined amount; and
   means for registering said warning signal to indicate a significant alteration in the patient's lung compliance.

* * * * *